United States Patent [19]

Bistrian et al.

[11] Patent Number: 5,320,846
[45] Date of Patent: Jun. 14, 1994

[54] METHOD AND COMPOSITION FOR TESTING PATIENTS WITH METABOLIC DEPLETING DISEASES

[75] Inventors: Bruce R. Bistrian, Ipswich; John D. Palombo, Medfield, both of Mass.

[73] Assignee: New England Deaconess Hospital Corp., Boston, Mass.

[21] Appl. No.: 965,609

[22] Filed: Oct. 22, 1992

Related U.S. Application Data

[63] Continuation of Ser. No. 686,590, Apr. 17, 1991, abandoned.

[51] Int. Cl.$^5$ .............................................. A61K 47/00
[52] U.S. Cl. ..................................... 424/439; 514/46; 514/838; 514/893; 514/894
[58] Field of Search .................. 424/439; 514/46, 838, 514/893, 894

[56] References Cited

U.S. PATENT DOCUMENTS

| | | | |
|---|---|---|---|
| 3,686,392 | 8/1972 | Hamada | 424/442 |
| 3,819,830 | 6/1974 | Yoshimura | 514/893 |
| 4,758,553 | 7/1988 | Ogoshi | 514/48 |
| 4,880,783 | 11/1989 | Mentzer | 514/46 |
| 4,994,442 | 2/1991 | Gil | 514/885 |

OTHER PUBLICATIONS

Palombo et al. (Doctoral Thesis) "Enhanced Restoration of Adenine Nucleotides . . . " Nutrition Research Labs (1990).
Palombo et al., "Glycolytic Support of Adenine Nucleotides . . . " Transplantation, vol. 48, 901–905 (1989).
Ogoshi et al., "Effect of a Nucleoside-Neclleotide Mixture . . . " Nutrition, vol. 5, No. 3 (May/Jun. 1989).
Palombo et al., "Decreased Loss of Liver Adenosine . . . " Gastroenterology, American Gastroenterological Association, 95:1043–0 (1988).
Lee et al., "Liver Adenosine Triphosphate and pH . . . " Liver, 8:3370343 (1988).
Ogoshi et al., "Effects of Total Parenteral Nutrition . . . " Journal of Parenteral & Enternal Nutrition, vol. 12, No. 1 (1988).
Leleiko et al., "Tissue-Specific Gene Expression Results . . . " American Gastroenterological Association, Gastroenterology, 93:1014–1020 (1987).
Gores et al., "The Isolated Perfused Rat Liver . . . " Hepatology, vol. 6, No. 2, 511–514 (1986).
Ogoshi et al., "Effect of Nucleotide and Nucleoside Mixture . . . " Journal of Parenteral and External Nutrition, vol. 9, No. 3 (1985).
Carr et al., "Quantitative Semi–Automated Enzymatic . . . " Communative Biochemistry & Physiology, (1984).
Savaiano et al., "Adenine, The Precursor of Nucleic Acids . . . " J. Nutri., 111:1816–1822 (1981).
Lowry et al., "Protein Measurement with the Folin . . . " JBC, 193 (1951).

Primary Examiner—D. Gabrielle Phelan
Attorney, Agent, or Firm—Lahive & Cockfield

[57] ABSTRACT

A method of treating patients with clinical disorder involving splanchnic disorders such as liver or gut dysfunction, the dysfunction being characterized by depletion of metabolic energy sources. The treatment involves the step of administering an effective amount of adenosine, or related nucleosides, to achieve and/or maintain normal metabolic levels of adenosine triphosphate (ATP) and/or its precursors in the patient's liver or other splanchnic organs. Administration may be as a total enteral nutritional diet, or as a dietary supplement. The invention includes a total enteral nutrition diet having nutritionally acceptable amounts of a lipid source, a protein source, a carbohydrate source, a vitamin source, and a mineral source, and an effective amount of adenosine to achieve normal metabolic levels of ATP and/or its precursors in ATP deficient organs of a recipient host.

13 Claims, 4 Drawing Sheets

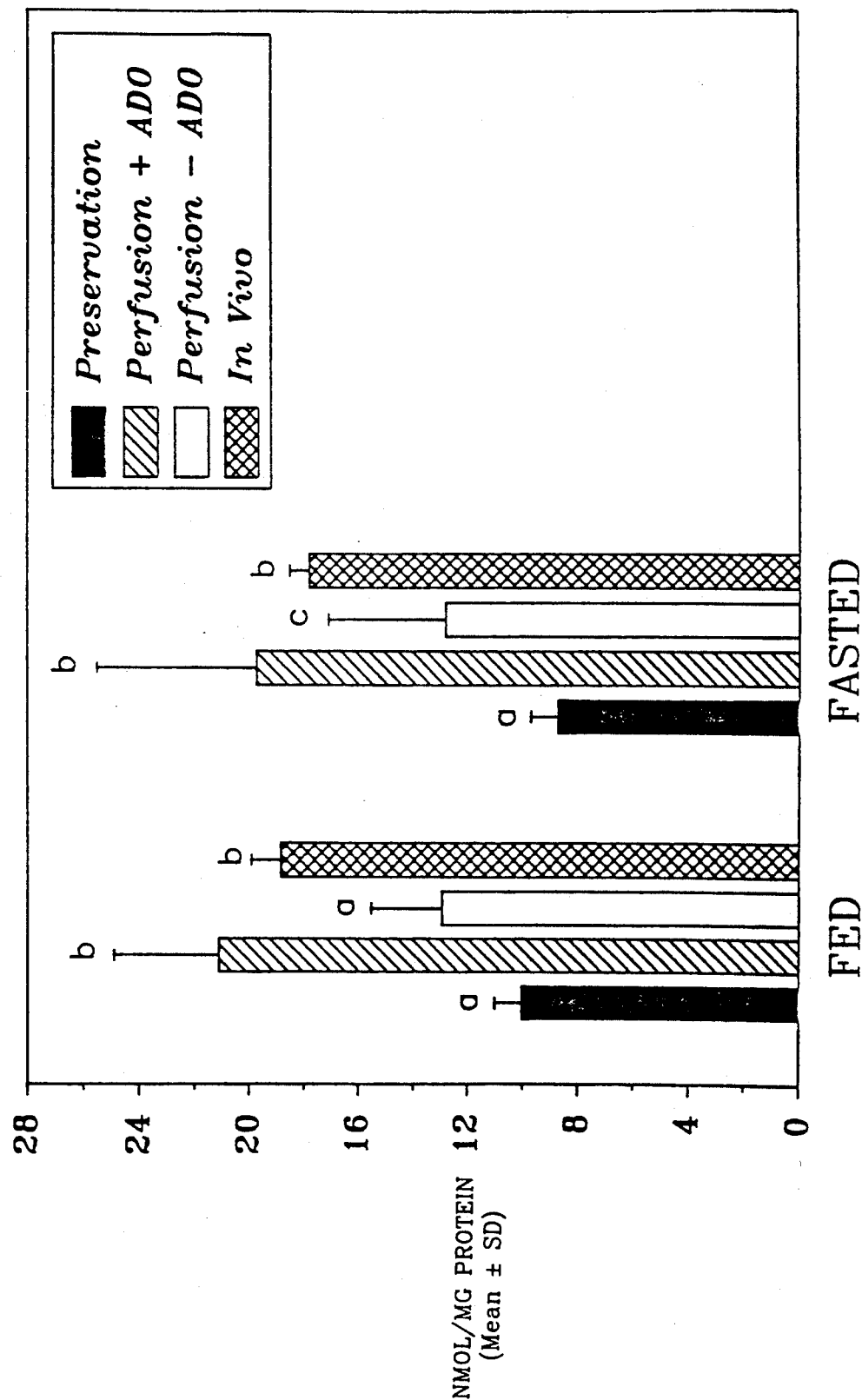

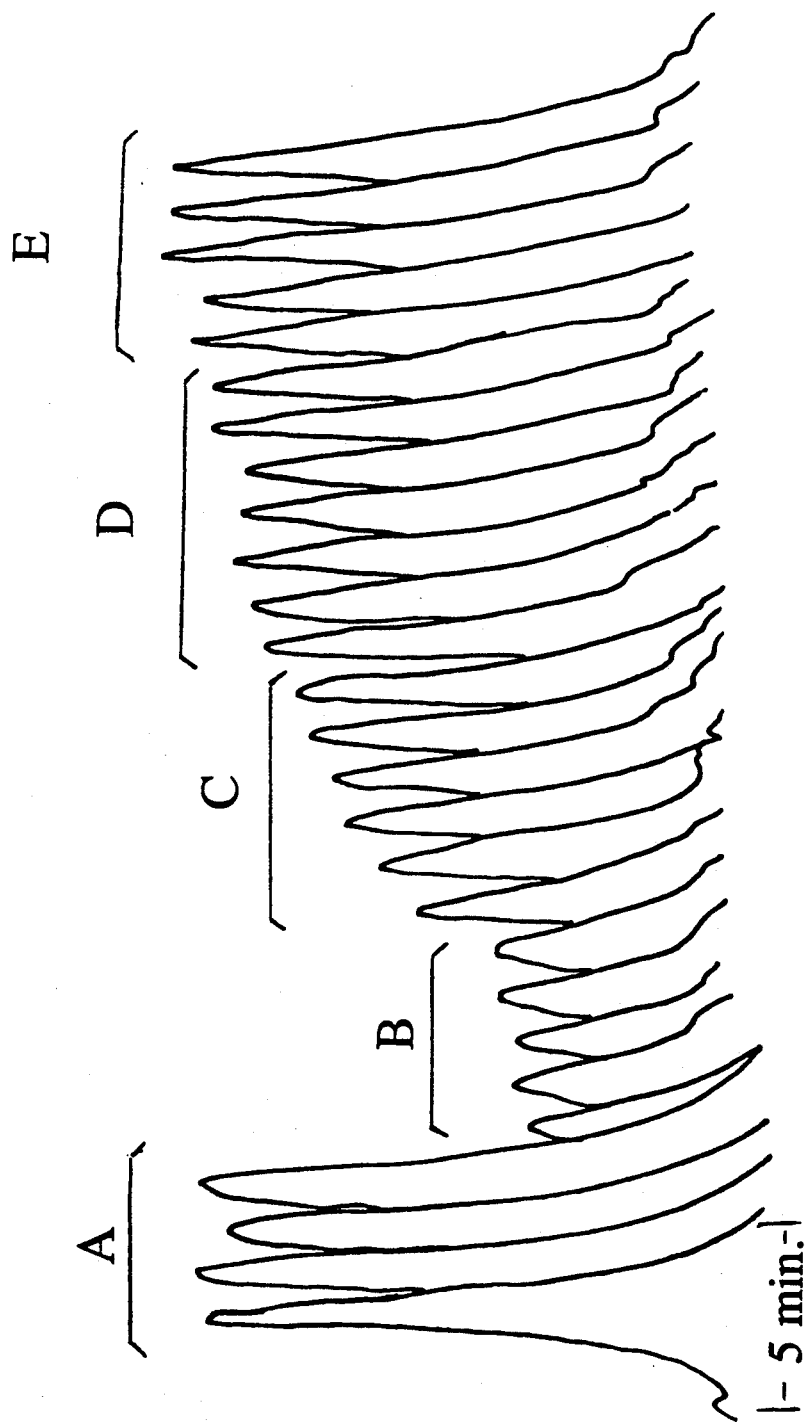

METHOD AND COMPOSITION FOR TESTING PATIENTS WITH METABOLIC DEPLETING DISEASES

This application is a continuation of application Ser. No. 686,590, filed Apr. 17, 1991, now abandoned.

BACKGROUND OF THE INVENTION

The present invention relates to enteral administration of adenosine and related nucleosides for restoration of adenosine triphosphate (ATP) and other energy substrates in splanchnic tissue following trauma, ischemia, and other conditions which compromise organ bioenergetic substrates.

Vasoconstriction of the major vessels of the splanchnic bed is one of the pathophysiologic events arising from gram-negative bacterial sepsis and shock. This event may also occur during surgical procedures involving these organs. Splanchnic organs normally have a low ambient $pO_2$, and would therefore be susceptible to ischemic injury during septic or other types of shock. This hypoperfused state leads to tissue ischemia and build-up of lactate due to reduced pyruvate entry into the Krebs cycle for oxidative phosphorylation. The energy substrate content of a given organ may therefore be compromised during ischemic episodes by: (1) reduced capacity for ATP regeneration; and/or (2) increased ATP utilization.

If severe enough, these imbalances which arise during ischemic episodes could foster extensive dephosphorylation of ATP and other nucleotides to yield purine nucleosides or nucleobases (i.e., purines). The purines could then be irreversibly degraded or released due to their membrane permeable nature. Given that de novo synthesis of purines requires energy nd a variety of substrates, restoration of ATP in ischemic splanchnic tissues is presumably retarded.

For some organs, particularly the gut, de novo synthetic pathways for purines normally are not operative given the availability of purines in foods. Unfortunately, anorexia which accompanies infection or postsurgical stress diminishes food intake. As a consequence, post-ischemic recovery of gut tissue ATP could be retarded due to the reduced purine intake coupled with a reduced capacity of the gut for de novo purine synthesis. This may promote a leakiness in the gut wall and increase the potential for bacterial or endotoxin translocation.

Furthermore, intestinal tissues, such as the gut, normally rapidly turn over as enterocytes are sloughed off into the lumen. This rapid turnover places a great demand for ATP on gut tissue. In septic or traumatized states, therefore, reduced tissue content of ATP could retard enterocyte formation.

These catabolic events would foster conditions which enable bacterial or endotoxin translocation across the damaged or weakened gut wall. In the immune-compromised septic or post-operative patients, this condition could precipitate multiple organ failure.

Allograft liver dysfunction during post-transplant recovery is life-threatening, requiring re-transplantation or prolonged intensive care. Although the etiology of this dysfunction is unknown, liver synthetic function is retarded by a limited ATP supply. Extensive degradation of ATP (over 85%) during liver storage, coupled with the washout of salvageable precursors prior to implantation may render the liver conditionally deficient in ATP precursors and retard post-transplant ATP recovery.

In organ transplant situations, reduced ATP often inhibits successful transplant. Recent evidence indicates that the primary injury to the donor liver is associated with disruption of the sinusoidal endothelium during hypothermic preservation. Subsequent reperfusion injury to hepatocytes results from localized ischemia arising from microcirculatory disturbances. Prior to these events, liver adenine nucleotide content is substantially reduced within the first 4 hours of storage ex vivo. Since nucleotide synthesis de novo is both energy and substrate dependent, restoration of total adenine nucleotide content through the de novo pathway could be retarded by the decreased availability of ATP following preservation.

The release of salvageable precursors from the allograft liver during reflow can produce a conditional deficiency of substrates to further impede ATP recovery. A reduction in ATP synthetic capacity coupled with poor oxygenation during reflow could exacerbate parenchymal and nonparenchymal cell damage.

Exogenous adenosine is an effective substrate capable of augmenting or supporting hepatocellular ATP concentrations in vivo or in vitro. Exogenous adenosine has also been utilized to maintain ATP concentrations in dog liver subjected to extend perfusion preservation A recent study reports a correlation of ATP recovery with hepatocellular viability. In a similar fashion, perfusion of mouse livers with the nucleobase adenine following the imposition of 20 minutes of ischemia restored ATP concentrations to pre-ischemic levels, whereas ATP recovery in livers perfused without adenine was only 63% of normal.

There remains a need for an improved method of increasing energy levels of splanchnic tissue. Especially in transplant situations, organs have depleted energy stores and cannot de novo produce required metabolic energy.

Accordingly, it is an object of the invention to provide an improved method for increasing ATP levels in patients suffering from a form of splanchnic disorder.

It is another object of the invention to provide a total enteral nutrition diet for achieving and maintaining normal metabolic levels of ATP in a patient.

Another object is to provide improved absorptive capacity and intestinal tolerance to enteral feeding.

Yet another object is to provide adenosine with the other components of a complete diet to improve absorptive capacity and intestinal tolerance to enteral feeding. Other objects, features, and advantages of the invention will be apparent from the following drawings, description of the preferred embodiments, and from the claims.

SUMMARY OF THE INVENTION

The present invention generally relates to a method and composition for treating metabolic energy depletion in patients suffering from splanchnic, such as liver or gut, dysfunction by enteral introduction of specific nucleosides.

Specifically, the invention involves a method of treating a patient with a clinical disorder involving splanchnic disorders such as liver or gut dysfunction, the dysfunction being characterized by depletion of energy sources. The treatment involves the step of enterally administering an effective amount of adenosine, or a related nucleoside, to achieve and/or maintain normal metabolic levels of adenosine triphosphate (ATP) in a patient's liver. The administered nucleoside may be adenosine, guanosine, or inosine. The method may also be effective in achieving normal metabolic levels of ATP precursors, such as ADP. The patient may suffer from a clinical liver dysfunction or trauma such as ischemia, trauma, sepsis, malnutrition, liver surgery, hepatitis, or liver transplant. Alternatively, the patient may suffer from gut dysfunctions such as those involving malnutrition, ischemia, trauma, sepsis, chemotherapy, radiotherapy, or surgery. The amounts useful to achieve the metabolic normal levels of ATP are well known to those skilled in the art.

The adenosine, or related nucleosides, may be administered as part of a total enteral nutrition formulation, or as a dietary supplement. The adenosine may be administered as part of a sustained release vehicle which degrades over time to release the entrapped adenosine. Providing adenosine, or a related nucleoside, in accordance with he method of the present invention enables splanchnic tissues to more rapidly regenerate ATP or other related molecules during or following shock or trauma. The amount of adenosine useful in practicing the invention ranges from about 10 mg to about 200 mg per hour. The exact range depends on individual factors for each patient.

The present invention further involves a total enteral nutrition diet having nutritionally acceptable amounts of a lipid source, a protein source, a carbohydrate source, a vitamin source, and a mineral source. The invention specifically involves the addition of adenosine, or one of its related nucleosides, to the diet. The amount of nucleoside in the diet is sufficient to achieve and maintain normal metabolic levels of ATP or its precursors in ATP deficient organs of the recipient. The exact useful amount is well known to those skilled in the art. This diet is typically used in the method of the invention, but may also be used for individuals not suffering from acute ATP deficiency.

BRIEF DESCRIPTION OF DRAWINGS

FIG. 3 is a bar graph representation of total adenine nucleotide (TAN) concentrations (mean±standard deviation nmol/mg protein) of rat livers following 30 minutes of perfusion with modified Krebs-bicarbonate buffer containing 20% v/v fluorocarbon-43.

FIG. 4 is a composite spectrum of individual Nuclear Magnetic Resonance (NMR) measurements of ATP, using the signal from $^{31}P$, in a rat liver over time.

DETAILED DESCRIPTION OF PREFERRED EMBODIMENT

Figure 1:
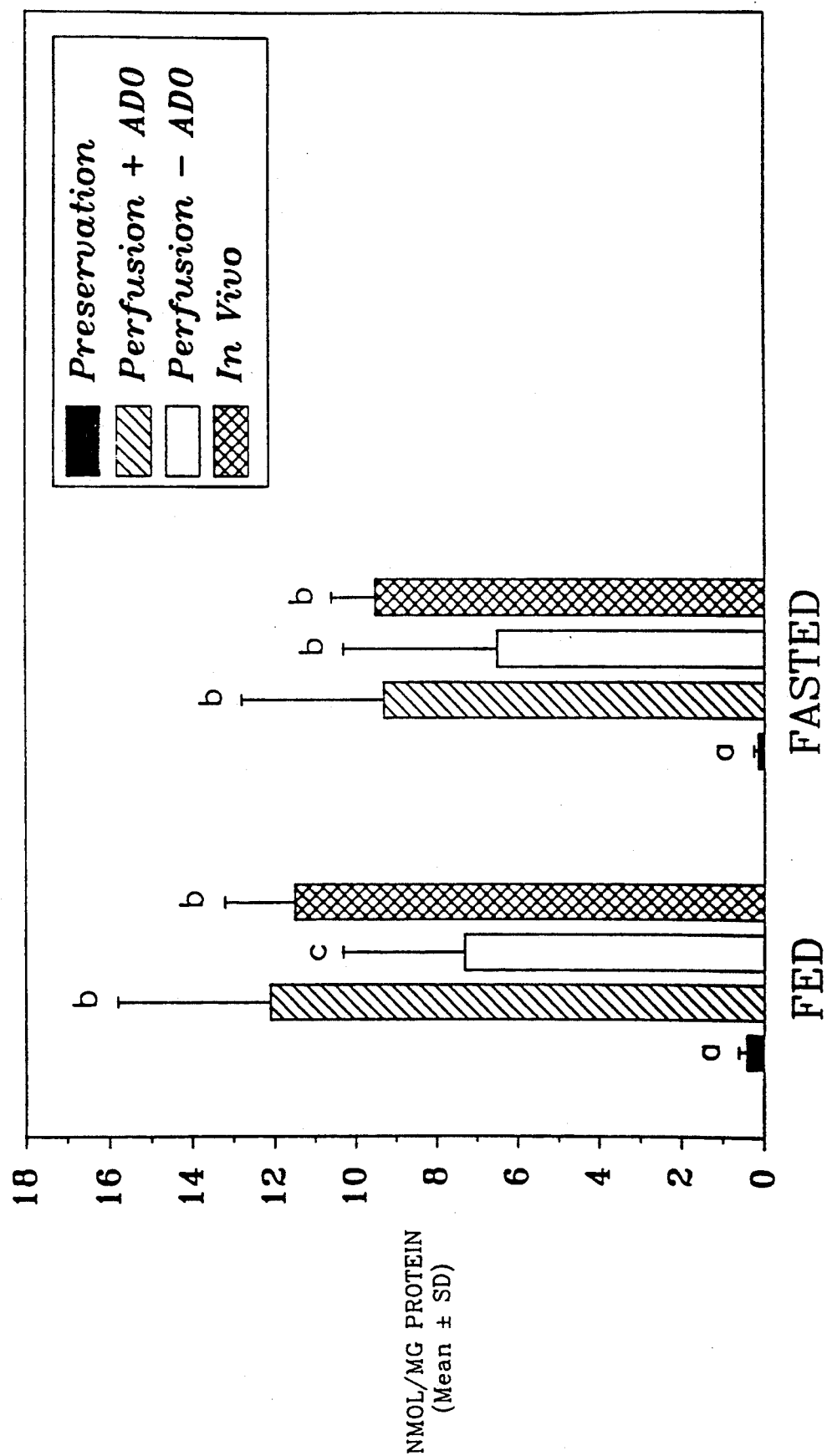
FIG. 1 is a bar graph representation of adenosine triphosphate (ATP) concentrations (mean±standard deviation nmol/mg protein) of rat livers following 30 minutes of perfusion with modified Krebs-bicarbonate buffer containing 20% v/v fluorocarbon-43.

The present invention generally relates to providing adenosine, or one of its related nucleosides, in an enteral feeding regimen which enables splanchnic tissues to more rapidly generate ATP, or other related nucleotides, during or following shock or trauma, including post-transplant situations.

Since it is not phosphorylated, adenosine is membrane-permeable, which enables effective enteral administration. Adenosine is not susceptible to substantial degradation in the alimentary or digestive track, but is absorbable by the gut. Since it is absorbed directly into the blood stream by the tissue, the adenosine can relatively gradually be introduced to the gut and liver, avoiding bolus introduction to the vascular system. Enteral administration is particularly advantageous in situations where a patient is not or cannot be on a parenteral diet, e.g., immediately following organ transplant, or where a parenteral diet is less effective, for example, to prevent bacterial translocation from the intestine after injury or sepsis.

Enhanced restoration of tissue nucleotides by enteral supplementation with adenosine improves synthetic function, cell repair, and recovery of cell homeostatic mechanisms (e.g., reestablishment of ion gradients). Given the compromised energy content and impaired synthetic capacity of liver during chronic ischemia or end-stage liver disease, provision of adenosine would preclude the need for the liver to simultaneously synthesize both adenine and ribose. These two components are synthesized by separate metabolic processes which require additional substrates potentially lacking in the diseased liver.

Thus, the enteral administration of adenosine, or related nucleosides such as guanosine and inosine, may be effective in patients with marginal liver function (i.e., impaired hepatic synthetic capacity) or in patients who receive a liver transplant. In most instances, liver dysfunction may arise from ischemia, trauma, sepsis, malnutrition, or surgery. Another use for the enteral nutritional system of the present invention is in patients who are receiving anti-metabolite chemotherapy and who have lost their capacity to either synthesize adenine nucleotides de novo or salvage adenine nucleotide precursors.

For the gut in particular, enteral provision of adenosine may improve gut barrier function by replenishing the energy substrates of enterocytes while fostering enterocyte formation. The method of the present invention may be used with patients who have gut dysfunction. Such dysfunctions typically arise from malnutrition, ischemia, trauma, sepsis, chemo- or radiotherapy, or surgery.

In practicing the method of the invention, adenosine, or a related nucleoside, is enterally administered in a dosage that is dependent upon the route of administration. Approximately 10-200 mg adenosine or related nucleoside may be continuously enterally administered each hour for the average adult recipient. Use in children is adjusted according to body weight.

The adenosine may also be administered as a total enteral nutrition diet. In that instance, the diet would consist essentially of a lipid source, a protein source, a vitamin source, a carbohydrate source, and a mineral source. Lipid sources could be from vegetable oil, fish oil or combinations that at least provide adequate amounts of essential fatty acids, e.g., linoleic or alpha linolenic acids, as well as other omega-3 or omega-9 fats.

Protein sources could be whole protein (e.g., albumin, casein, soy partial protein hydolysates or crystalline amino acids. Carbohydrates could be simple monosaccharides, disaccharides, oligosaccharides, or complex carbohydrates. The adenosine and related nucleosides may also be incorporated into a diet as a dietary supplement. In that instance, the respective doses may be in the range of 10 to 200 mg/hour.

The invention is further described in the following non-limiting examples.

EXEMPLIFICATION

EXAMPLE 1

The following example demonstrates the effect of exogenous adenosine on ATP and ADP levels in the liver.

Adult male Sprague-Dawley rats (210-250 g) were randomized to be either chow-fed ad libitum or fasted for 48 hours prior to liver harvesting (n=10 each). Subsequently, each rat was anesthetized with ether and the portal vein was cannulated with 0.025" ID silastic tubing. The liver was then flushed with 25 ml of cold University of Wisconsin (UW) solution (2° C.) which was devoid of antibiotics and insulin. The hepatic artery, infrahepatic vena cava, and portal vein distal to the portal flush line were ligated immediately prior to the flush. The superior vena cava was severed to facilitate flushing.

Following the flush, the liver was excised, weighed, and stored in 40 ml of cold UW solution for 20 hours of hypothermic (2° C.) preservation. To establish baseline concentrations of substrates at the end of 20 hours of preservation, a second group of rats was treated identically as above, and liver samples were obtained after 20 hours of storage in UW solution for determination of adenine nucleotide, protein, glycogen, and lactate concentrations as described below.

The isolated perfused rat liver model was utilized to assess adenine nucleotide recovery following preservation, as described in G. J. Gores, et al. "The Isolated Perfusad Rat Liver: Conceptual and Practical Considerations", Hepatology 6:511 (1986). The perfusate consisted of a modified Krebs-bicarbonate buffer which contained 20% (v/v) fluorocarbon-43, available from Alpha Therapeutic Corporation, Los Angeles, Calif., as an oxygen carrier. The concentrations of the remaining components of the perfusate were: 120 mEq/l sodium chloride, 4.5 mEq/l potassium phosphate, 2.4 mEq/l magnesium sulfate, 23 mEq/l sodium bicarbonate, and 10 mM glucose.

The perfusate (pH=7.4 at 30° C.) was bubbled with $O_2:CO_2$ (95:5) for 30 minutes prior to and throughout the perfusion period. The mean (±SD) pO2 of the perfusate in the bubbling flask was 573±30 mmHg. A Physiologic flow rate of 1.25 ml/g/min was utilized to avoid metabolic alterations that occur at higher flow rates. Based upon random selection, half (n=5) of the livers from each dietary group were perfused with Perfusate to which 1 mM adenosine has been added.

Following preservation, each liver was initially perfused with the modified Krebs-fluorocarbon solution at half rate for two minutes to remove the UW solution, which was discarded. Non-recirculating perfusion of the livers was accomplished using a Masterflex pump fitted with an 8 roller Ismatec minicartridge pump head and a variable speed controller, both the pump and the minicartridge available from Cole-Parmer, Chicago, Ill. Once the perfusion rate was established, little adjustment was required during perfusion. The liver and perfusate were kept at 30° C. Each liver was perfused for 30 minutes at the physiologic flow rate prior to freeze-clamping of two lobes for tissue analysis.

Tissue nucleotides were determined by High Performance Liquid Chromatography (HPLC), as described by J. D. Palombo, et al., "Decreased Loss of Liver ATP During Hypothermic Preservation in Rats Pretreated with Glucose: Implications for Organ Donor Management", Gastroenterology 95:1043 (1988). The adenosine content of the UW solution was also verified to be 5 mM by HPLC, confirming the supplier's formulation (DuPont Critical Care, Bannockburn, Ill.). Tissue lactate was measured enzymatically at 340 nm by monitoring the conversion of NAD+ to NADH in the supernatant of deproteinized liver. The protein content of liver was determined by the Lowry method (O. H. Lowry; Rosebrough, N. H.; Farr, A. L.; Randall, R. J., "Protein Measurement with Folin Phenol Reagent", J. Biol. Chem. 193:265 (1951)). Liver glycogen was calculated from the amount of glucose released by treatment of homogenized tissue with amyloglucosidase following determination of the free glucose content (see R. S. Carr; Neff, J. M., "Quantitative Semi-automated Enzymatic Assay for Tissue Glycogen", Comp. Biochem. Physiol. 77:447 (1984)). The nucleotide, lactate, glycogen, and protein measurements obtained on each of the two freeze-clamped lobes were averaged prior to statistical analysis. Perfusate Na+, K+, and Cl—were measured by an Astra-8 analyzer, available from Beckman Instruments, Fullerton, Calif.

Computer-based statistical programs were utilized, available from BMDP Software, Inc., Los Angeles, California. Statistical tests included 2-way ANOVA by diet and treatment (i.e., with or without adenosine). Levene's test provided a test of equal variability among the cells. If the Levene test was significant, the Brown-Forsythe test was used to allow for unequal group variances at the expense of a loss of degrees of freedom. If the overall ANOVA or Brown-Forsythe test was significant ($p<0.05$), post hoc comparisons of means were determined using Student's t tests.

As expected, the liver weights of the chow-fed rats ($X \pm SD = 10.6 \pm 0.9$ g) were significantly greater ($p<0.001$) than those of the fasted rats ($7.0 \pm 0.7$ g) at the time of harvesting. Within each dietary group, liver weights were similar for the two perfusion treatment groups (i.e., with or without adenosine).

The mean oxygen delivery to the fed (n=10) and fasted (n=10) livers during Perfusion was similar (overall $X \pm SD = 2.10 \pm 0.11$ μmol $O_2$/g liver/min). No differences in oxygen delivery existed between the two perfusion treatment groups (i.e., with or without adenosine). Oxygen consumption, based upon measurements obtained after 20 minutes of perfusion, was also similar within each dietary and treatment group (overall $X \pm SD = 1.05 \pm 0.21$ μmol/g/min). Thus, 50% of the $O_2$ delivered was extracted and utilized by the perfused livers, approximating the consumption expected at 30° C.

Figure 2:
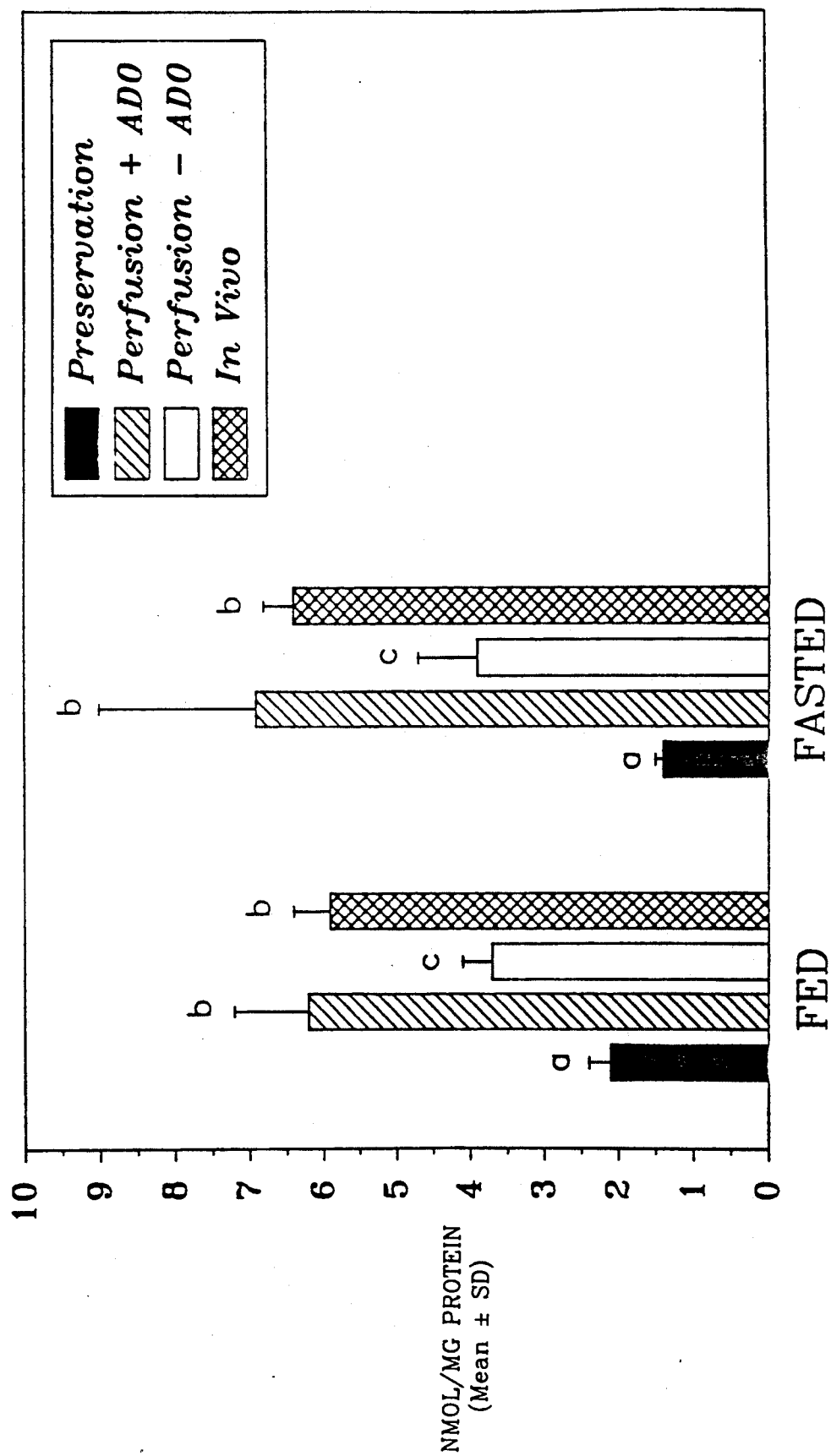
FIG. 2 is a bar graph representation of adenosine diphosphate (ADP) concentrations (mean±standard deviation nmol/mg protein) of rat livers following 30 minutes of perfusion with modified Krebs-bicarbonate buffer containing 20% v/v fluorocarbon-43.

FIGS. 1 and 2 summarize the concentrations (nmol/mg protein) of the individual adenine nucleotides, ATP and ADP, respectively, both in the livers which served as preservation controls (i.e., 20 hours of storage in UW) and in the livers perfused for 30 minutes following 20 hours of preservation. For comparative purposes, the physiologic concentrations in vivo for each nucleotide in livers from rats subjected to similar dietary conditions are described in J. D. Palombo; Pomposelli, J. J.; Hirschberg, Y.; Blackburn, G. L.; Bistrian, B. R., "Glycolytic Support of Adenine Nucleotides in Rat Liver Flush-preserved with UW or Collins' II", Transplantation 48:901 (1989).

The rats were either chow-fed or fasted (n=10 in each group) for 48 hours prior to harvesting the livers, which were then flushed and preserved for 20 hours in UW solution. Within each dietary group (i.e., chow-fed or fasted), livers were perfused with with 1 mM adenosine added to (+) or omitted from (−) the perfusate. Preservation control values were obtained from a second set of rate treated identically without subsequent perfusion.

As illustrated in FIG. 1, ATP concentrations at the end of the preservation period were severely reduced relative to levels in vivo. FIG. 1 is a bar graph representation of ATP concentrations (mean±SD), expressed as nmol ATP per mg protein. Differences between the two dietary groups were not evident. After 30 minutes of perfusion, ATP concentrations of all livers perfused with adenosine added to the perfusate were restored to levels found in vivo. irrespective of the livers' prior nutritional status. Livers from fed rats perfused without adenosine had significantly lower ($p<0.05$) ATP concentrations than either livers perfused with adenosine or livers in vivo. A similar trend was found for the perfused livers from fasted rats, except that there were no statistically significant differences between the two perfusion treatment groups and levels in vivo.

FIG. 2 illustrates that ADP concentrations in all livers following preservation were significantly decreased relative to ADP levels in vivo ($p<0.001$). FIG. 2 is a bar graph representation of ADP concentrations (mean±SD), expressed as nmol ADP per mg protein. ADP content of livers perfused with adenosine was completely restored to levels found in vivo regardless of prior dietary treatment. In comparison, ADP concentrations in livers which were perfused without adenosine were only 60% of normal ($p<0.001$) irrespective of their prior nutritional status.

Extended preservation severely reduced the total adenine nucleotide (TAN) concentrations relative to TAN concentrations in vivo as illustrated in FIG. 3, wherein FIG. 3 is a bar graph representation of total adenine nucleotide (TAN) concentrations (mean±SD), expressed as nmol adenine nucleotides per mg protein. TAN concentrations of fed and fasted liver following preservation were 53% and 49%, respectively, of levels in vivo. In response to the increased concentrations of ATP (FIG. 1) and ADP (FIG. 2), the TAN content of all livers perfused with adenosine had increased significantly (mean=20 nmol/mg protein, $p<0.01$) to normal physiologic concentrations within 30 minutes of perfusion. In contrast, TAN concentrations of all livers perfused without adenosine remained significantly lower (mean=13 nmol/mg protein, $p<0.02$) than levels in vivo irrespective of dietary grouping.

Lactate concentrations in livers from chow-fed rats were significantly greater than those in livers from fasted rats (5.4 versus 2.6 μmol/g liver, $p<0.001$) following preservation. The increased production of lactate in flush-preserved livers harvested from fed rats was indicative of enhanced glycolysis. Following perfusion, lactate concentrations in livers from chow-fed rats remained elevated relative to those in livers from fasted rats (2.6 versus 1.6 μmol/g liver, $p<0.01$), irrespective of the presence or absence of adenosine in the perfusate.

As demonstrated, the use of exogenous adenosine restores both ATP, ADP, and TAN levels to about normal in vivo levels. Livers preserved in UW and reperfused without adenosine were unable to fully restore intracellular ATP, ADP or TAN content. These results indicate that a conditional deficiency of ATP precursors limits ATP restoration in reperfused liver subjected to ischemic conditions.

EXAMPLE 2

Fresh rat livers from 12 adult Sprague-Dawley (SD) rats were harvested and portally perfused with oxygenated Krebs buffer at 37° C. $^{31}$P Nuclear Magnetic Resonance (NMR) spectra at 121.6 MHz were acquired over 30 minutes and baseline ATP determined from the area of the B-ATP peak. Livers were then flushed with University of Wisconsin Preservation Solution, available from Dupont Critical Care, Chicago, Ill., and stored for 18 hours at 4° C. Subsequently, all livers were reperfused with oxygenated Krebs for 30 minutes to determine initial ATP recovery by NMR. Over the next 90 minutes, livers were perfused with either Krebs (−) or Krebs (+) containing lmM adenosine (ADO). ATP restoration, expressed as a percentage (mean +/− standard deviation) of the prestorage baseline level was as follows:

|  | Reperfusion Time (min) | | | | |
| --- | --- | --- | --- | --- | --- |
|  | 15 | 30 | 60 | 90 | 120 |
| −ADO (n = 6) | 64 ± 20 | 61 ± 15 | 56 ± 14 | 53 ± 14 | 52 ± 16 |
| +ADO (n = 6) | 53 ± 8 | 51 ± 8 | 82 ± 8 | 101 ± 13 | 112 ± 15 |

Adenosine (ADO) was supplemented in the +ADO livers having reperfusion times of 60, 90, and 120 minutes. Using a Students t test, these differed from −ADO livers, $p<0.01$ for the supplemented livers taken at 60 minutes, while $p<0.001$ for supplemented livers taken at times 90 and 120 minutes.

The mean ATP recovery during the initial 30 minutes reperfusion was less than 60%, having a statistical p value $p<0.001$ of pre-storage baseline. Subsequent adenosine supplementation promoted full recovery of liver ATP. ATP content of livers which did not receive adenosine decreased to 52% of the baseline. These data indicate that a deficiency of ATP precursors limits ATP recovery and stabilization in donor livers after ischemic storage. Given that the blood content of adenosine is normally low (0.4 μM), a post-transplant dietary requirement for adenosine or other nucleotide precursors may exist. Enterally administered adenosine could enhance ATP restoration and liver function in allograft livers.

EXAMPLE 3

For this example, results were obtained from five series of tests. Each series represents four or more sequential five minute measurements of the ATP content of rat liver. Measurements were made using NMR readings of the signal from $^{31}$P previously introduced by standard methods. The results of this Example are shown in FIG. 4, wherein the illustrated Peaks represent relative levels of ATP comparable to the in vivo state of the liver.

The liver of a Sprague-Dawley rat was excised and immediately perfused with oxygenated Kreb's buffer solution. The data for this period is shown as Series A. The liver was then hypothermically preserved for 18.5 hours, then again reperfused for 25 minutes with oxygenated Krebs. The data for this period is shown as Series B. Adenosine (1 mM) was then added to the Krebs buffer and the liver was reperfused for 30 minutes, resulting in the data for Series C. Following Series C, the Krebs±Adenosine perfusate was replaced with Krebs alone, giving the Series D results. Finally, Krebs-+adenosine was reperfused for 25 minutes (Series E).

As shown in FIG. 4, the restoration of ATP in Series B, following reperfusion with oxygenated Krebs, was only 40% relative to Series A. The addition of adenosine for Series C increased the area of peaks and, therefore, indicates an increase in the amount of intracellular ATP. The relative amount of ATP in Series C was double that of Series B, and was approximately 80% of the in vivo amount shown in Series A. When the Krebs-plus-adenosine solution was replaced with Krebs alone, for Series D, there was a small relative increase in the ATP peak areas. Most importantly, Series D data demonstrates that the ATP gained during perfusion with Krebs-plus-adenosine was retained in the liver when adenosine was removed. Reintroduction of the Krebs-plus-adenosine solution for Series E data shows no further increase in the ATP peak areas. By the end of Series E, the amount of ATP equaled that in Series A.

As shown, hypoxic liver can become deficient in nucleotide precursors to the extent that restoration of ATP during reperfusion is retarded. Once adenosine was provided and incorporated into ATP, subsequent removal of adenosine did not affect the ATP content. Thus, adenosine can become a conditionally essential substrate for restoration of ATP in splanchnic organs. This example further demonstrates that adenosine can safely and efficaciously be provided by the enteral administration route.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of replenishing gut ATP and ADP in a patient with reduced ADP or ATP levels due to gut dysfunction, said method comprising the step of enteral administration of an effective amount of a single nucleoside selected from the group consisting adenosine, inosine and guanosine, wherein said effective amount of said single nucleoside ranges from about 10 to about 200 milligrams per hour.

2. The method of claim 1 wherein said patient consists of a patient having a disorder selected from the group consisting of malnutrition, ischemia, trauma, sepsis, chemotherapy, radiotherapy, and surgery.

3. The method of claim 1 wherein said single nucleoside is administered as part of a total enteral nutrition formulation comprising nutritionally acceptable amounts of a lipid source, protein source, a carbohydrate source, a vitamin source, and a mineral source.

4. The method of claim 1 wherein said single nucleoside is administered as a dietary supplement.

5. The method of claim 1 wherein said enteral administration of a said effective amount of said single nucleoside comprises administering a sustained release vehicle containing said single nucleoside wherein said sustained release vehicle degrades over time.

6. The method of claim 1 wherein said gut dysfunction further produces impaired protein synthesis in the gut.

7. The method of claim 1 wherein said selected single nucleoside is adenosine.

8. A method of increasing ATP and ADP levels in the liver of a patient with a liver disorder that reduces ADP or ATP levels, said method consisting essentially of the step of enteral administration of an effective amount of a single nucleoside selected from the group consisting of adenosine, guanosine and inosine, wherein said effective amount of said single nucleoside ranges from about 10 to about 200 milligrams per hour.

9. The method of claim 8 wherein said patient having said liver disorder comprises a patient having a disorder selected from the group consisting of ischemia, trauma, sepsis, malnutrition, liver surgery, hepatitis, and liver transplant.

10. The method of claim 8 wherein said effective amount of said single nucleoside is administered as an enteral dietary supplement.

11. The method of claim 8 wherein said enteral administration of said effective amount of said single nucleoside comprises administering a sustained release vehicle containing said single nucleoside wherein said sustained release vehicle degrades over time.

12. The method of claim 8 wherein said liver disorder produces impaired protein synthesis in the gut.

13. The method of claim 8 wherein said selected single nucleoside is adenosine.

* * * * *